(12) United States Patent
Bao et al.

(10) Patent No.: US 11,999,957 B2
(45) Date of Patent: Jun. 4, 2024

(54) **METHOD FOR ENHANCING VANILLIN RESISTANCE OF *SACCHAROMYCES CEREVISIAE* BY KNOCKING OUT SNG1 GENE**

(71) Applicant: QILU UNIVERSITY OF TECHNOLOGY, Shandong (CN)

(72) Inventors: Xiaoming Bao, Shandong (CN); Liyun Song, Shandong (CN); Xinning Wang, Shandong (CN); Wenyan Cao, Shandong (CN); Weiquan Zhao, Shandong (CN); Zailu Li, Shandong (CN)

(73) Assignee: QILU UNIVERSITY OF TECHNOLOGY, Jinan (CN)

( * ) Notice: Subject to any disclaimer, the term of this patent is extended or adjusted under 35 U.S.C. 154(b) by 549 days.

(21) Appl. No.: 17/118,179

(22) Filed: Dec. 10, 2020

(65) Prior Publication Data

US 2021/0388365 A1  Dec. 16, 2021

(30) Foreign Application Priority Data

Jun. 10, 2020 (CN) .......................... 202010527783.4

(51) Int. Cl.
| | | |
|---|---|---|
| *C12N 1/19* | (2006.01) | |
| *C07K 14/395* | (2006.01) | |
| *C12N 1/36* | (2006.01) | |
| *C12N 9/10* | (2006.01) | |
| *C12N 15/81* | (2006.01) | |
| *C12N 15/90* | (2006.01) | |
| *C12R 1/865* | (2006.01) | |

(52) U.S. Cl.
CPC ............ *C12N 15/81* (2013.01); *C07K 14/395* (2013.01); *C12N 1/36* (2013.01); *C12N 15/905* (2013.01); *C12R 2001/865* (2021.05)

(58) Field of Classification Search
None
See application file for complete search history.

(56) References Cited

FOREIGN PATENT DOCUMENTS

| CN | 101292028 A | 10/2008 | |
|---|---|---|---|
| CN | 102016022 A | 4/2011 | |
| CN | 111549073 A * | 8/2020 | ........... C07K 14/395 |

OTHER PUBLICATIONS

Park et al., J. Microbiol. Biotechnol. 25:50-56, 2015 (Year: 2015).*
Singh et al., Curr. Protein Pept. Sci. 18:1-11, 2017 (Year: 2017).*
Zhang et al., Structure 26:1474-1485, 2018 (Year: 2018).*
Grey et al., Mutation Research 346:207-214, 1995 (Year: 1995).*
EMBL database accession No. X47920, Jun. 2006, 1 page (Year: 2006).*
Güldener et al., Nucleic Acids Res. 24:2519-2524, 1996 (Year: 1996).*

* cited by examiner

*Primary Examiner* — David Steadman

(57) ABSTRACT

A method of enhancing vanillin resistance of *Saccharomyces cerevisiae*, including: knocking out SNG1 gene from a genome of *Saccharomyces cerevisiae*. This application further provides a mutant of SNG1 gene of *Saccharomyces cerevisiae* including the nucleotide sequence shown in SEQ ID NO: 1, where the sequence shown in SEQ ID NO: 1, from left to right, consists of a −18~+203 bp fragment of SNG1 gene of *Saccharomyces cerevisiae*, a nucleotide fragment of loxp-KanMX4-loxp and a +1446~+1644 bp fragment of the SNG1 gene of *Saccharomyces cerevisiae*.

2 Claims, 2 Drawing Sheets

Specification includes a Sequence Listing.

SEQUENCE LISTING

<160> NUMBER OF SEQ ID NOS: 11

<210> SEQ ID NO 1
<211> LENGTH: 2032
<212> TYPE: DNA
<213> ORGANISM: Artificial Sequence
<220> FEATURE:
<223> OTHER INFORMATION: synthetic

<400> SEQUENCE: 1
gccgtacaga gaacaaatat gactaaatcg gttggtgatg aagagtcaca gtacattgag    60

| | |
|---|---|
| gaccctagtt ttgcagcagc agctgcattt actggcggca gggacggggt ttcgtacagt | 120 |
| aatcagcgat ttgctgaggg ttccggccat tcttctgact tagcaaagtc attagaagac | 180 |
| tatcggcctc ctgatgaaaa gccgtcctca ttgtcatctg tagctgaagc ttcgtacgct | 240 |
| gcaggtcgac aacccttaat ataacttcgt ataatgtatg ctatacgaag ttattaggtc | 300 |
| tagagatctg tttagcttgc ctcgtccccg ccgggtcacc cggccagcga catggaggcc | 360 |
| cagaataccc tccttgacag tcttgacgtg cgcagctcag gggcatgatg tgactgtcgc | 420 |
| ccgtacattt agcccataca tccccatgta taatcatttg catccataca ttttgatggc | 480 |
| cgcacggcgc gaagcaaaaa ttacggctcc tcgctgcaga cctgcgagca gggaaacgct | 540 |
| cccctcacag acgcgttgaa ttgtccccac gccgcgcccc tgtagagaaa tataaaaggt | 600 |
| taggatttgc cactgaggtt cttctttcat atacttcctt ttaaaatctt gctaggatac | 660 |
| agttctcaca tcacatccga acataaacaa ccatgggtaa ggaaaagact cacgtttcga | 720 |
| ggccgcgatt aaattccaac atggatgctg atttatatgg gtataaatgg ctcgcgata | 780 |
| atgtcgggca atcaggtgcg acaatctatc gattgtatgg gaagcccgat gcgccagagt | 840 |
| tgtttctgaa acatggcaaa ggtagccgttg ccaatgatgt tacagatgag atggtcagac | 900 |
| taaactggct gacggaattt atgcctcttc cgaccatcaa gcattttatc cgtactcctg | 960 |
| atgatgcatg gttactcacc actgcgatcc ccggcaaaac agcattccag gtattagaag | 1020 |
| aatatcctga ttcaggtgaa atattgttg atgcgctggc agtgttcctg cgccggttgc | 1080 |
| attcgattcc tgtttgtaat tgtccttta acagcgatcg cgtatttcgt ctcgctcagg | 1140 |
| cgcaatcacg aatgaataac ggtttggttg atgcgagtga ttttgatgac gagcgtaatg | 1200 |
| gctggcctgt tgaacaagtc tggaaagaaa tgcataagct tttgccattc tcaccggatt | 1260 |
| cagtcgtcac tcatggtgat ttctcacttg ataaccttat ttttgacgag gggaaattaa | 1320 |
| taggttgtat tgatgttgga cgagtcggaa tcgcagaccg ataccaggat cttgccatcc | 1380 |
| tatggaactg cctcggtgag ttttctcctt cattacagaa acggcttttt caaaaatatg | 1440 |
| gtattgataa tcctgatatg aataaattgc agtttcattt gatgctcgat gagttttttct | 1500 |
| aatcagtact gacaataaaa agattcttgt tttcaagaac ttgtcatttg tatagttttt | 1560 |
| ttatattgta gttgttctat tttaatcaaa tgttagcgtg atttatattt tttttcgcct | 1620 |
| cgacatcatc tgcccagatg cgaagttaag tgcgcagaaa gtaatatcat gcgtcaatcg | 1680 |
| tatgtgaatg ctggtcgcta tactgctgtc gattcgatac taacgccgcc atccagtgtc | 1740 |
| gaaaacgagc tctcgagaac ccttaatata acttcgtata atgtatgcta tacgaagtta | 1800 |
| ttaggtgata tcagatccac tagtggccta tgcgggaaga aattacggta ttctcgtggc | 1860 |
| atgggttgcc ctcaatacat ccttgatgcc attttgtatg aagtttgcag gtaaaaaaat | 1920 |
| gcaaaaaaat gctatgcaag cagcagaagc cgctgtcgca gcagctaccc agcgtgctag | 1980 |
| ccgcccggca gaggccaata ctgataaaaa taacaacccg cccggaaatt aa | 2032 |

<210> SEQ ID NO 2
<211> LENGTH: 221
<212> TYPE: DNA
<213> ORGANISM: Artificial Sequence
<220> FEATURE:
<223> OTHER INFORMATION: synthetic

<400> SEQUENCE: 2

| | |
|---|---|
| gccgtacaga gaacaaatat gactaaatcg gttggtgatg aagagtcaca gtacattgag | 60 |
| gaccctagtt ttgcagcagc agctgcattt actggcggca gggacggggt ttcgtacagt | 120 |

```
aatcagcgat tgctgaggg ttccggccat tcttctgact tagcaaagtc attagaagac      180
tatcggcctc ctgatgaaaa gccgtcctca ttgtcatctg t                         221
```

<210> SEQ ID NO 3
<211> LENGTH: 199
<212> TYPE: DNA
<213> ORGANISM: Artificial Sequence
<220> FEATURE:
<223> OTHER INFORMATION: synthetic

<400> SEQUENCE: 3

```
gggaagaaat tacggtattc tcgtggcatg ggttgccctc aatacatcct tgatgccatt      60
ttgtatgaag tttgcaggta aaaaaatgca aaaaaatgct atgcaagcag cagaagccgc     120
tgtcgcagca gctacccagc gtgctagccg cccggcagag gccaatactg ataaaaataa     180
caacccgccc ggaaattaa                                                  199
```

<210> SEQ ID NO 4
<211> LENGTH: 1612
<212> TYPE: DNA
<213> ORGANISM: Artificial Sequence
<220> FEATURE:
<223> OTHER INFORMATION: synthetic

<400> SEQUENCE: 4

```
agctgaagct tcgtacgctg caggtcgaca acccttaata taacttcgta taatgtatgc      60
tatacgaagt tattaggtct agagatctgt ttagcttgcc tcgtcccgc cgggtcaccc     120 ggccagcgac atggaggccc agaatacccct ccttgacagt cttgacgtgc gcagctcagg    180
ggcatgatgt gactgtcgcc cgtacattta gcccatacat ccccatgtat aatcatttgc     240
atccatacat tttgatggcc gcacggcgcg aagcaaaaat tacggctcct cgctgcagac     300
ctgcgagcag ggaaacgctc ccctcacaga cgcgttgaat tgtccccacg ccgcgcccct     360
gtagagaaat ataaaggtt aggatttgcc actgaggttc ttcttttcata tacttccttt     420 taaaatcttg ctaggataca gttctcacat cacatccgaa cataaacaac catgggtaag     480
gaaaagactc acgtttcgag gccgcgatta aattccaaca tggatgctga tttatatggg     540
tataaatggg ctcgcgataa tgtcgggcaa tcaggtgcga caatctatcg attgtatggg     600
aagcccgatg cgccagagtt gtttctgaaa catggcaaag gtagcgttgc caatgatgtt     660
acagatgaga tggtcagact aaactggctg acggaattta tgcctcttcc gaccatcaag     720
cattttatcc gtactcctga tgatgcatgg ttactcacca ctgcgatccc cggcaaaaca     780
gcattccagg tattagaaga atatcctgat tcaggtgaaa atattgttga tgcgctggca     840
gtgttcctgc gccggttgca ttcgattcct gtttgtaatt gtccttttaa cagcgatcgc     900
gtatttcgtc tcgctcaggc gcaatcacga atgaataacg tttggttga tgcgagtgat     960 tttgatgacg agcgtaatgg ctggcctgtt gaacaagtct ggaaagaaat gcataagctt    1020
ttgccattct caccggattc agtcgtcact catggtgatt tctcacttga taaccttatt    1080
tttgacgagg ggaaattaat aggttgtatt gatgttggac gagtcggaat cgcagaccga    1140
taccaggatc ttgccatcct atggaactgc ctcggtgagt tttctccttc attacagaaa    1200 cggcttttc aaaaatatgg tattgataat cctgatatga ataaattgca gtttcatttg    1260
atgctcgatg agttttccta atcagtactg acaataaaaa gattcttgtt ttcaagaact    1320
tgtcatttgt atagttttttt tatattgtag ttgttctatt ttaatcaaat gttagcgtga    1380
```

```
tttatatttt ttttcgcctc gacatcatct gcccagatgc gaagttaagt gcgcagaaag    1440
taatatcatg cgtcaatcgt atgtgaatgc tggtcgctat actgctgtcg attcgatact    1500
aacgccgcca tccagtgtcg aaaacgagct ctcgagaacc cttaatataa cttcgtataa    1560
tgtatgctat acgaagttat taggtgatat cagatccact agtggcctat gc            1612
```

```
<210> SEQ ID NO 5
<211> LENGTH: 31
<212> TYPE: DNA
<213> ORGANISM: Artificial Sequence
<220> FEATURE:
<223> OTHER INFORMATION: synthetic

<400> SEQUENCE: 5
gccgtacaga gaacaaatat gactaaatcg g                                   31

<210> SEQ ID NO 6
<211> LENGTH: 61
<212> TYPE: DNA
<213> ORGANISM: Artificial Sequence
<220> FEATURE:
<223> OTHER INFORMATION: synthetic

<400> SEQUENCE: 6
attaagggtt gtcgacctgc agcgtacgaa gcttcagctg acagatgaca atgaggacgg    60
c                                                                    61

<210> SEQ ID NO 7
<211> LENGTH: 66
<212> TYPE: DNA
<213> ORGANISM: Artificial Sequence
<220> FEATURE:
<223> OTHER INFORMATION: synthetic

<400> SEQUENCE: 7
gaagttatta ggtgatatca gatccactag tggcctatgg ggaagaaatt acggtattct    60
cgtggc                                                               66

<210> SEQ ID NO 8
<211> LENGTH: 32
<212> TYPE: DNA
<213> ORGANISM: Artificial Sequence
<220> FEATURE:
<223> OTHER INFORMATION: synthetic

<400> SEQUENCE: 8
ttaatttccg ggcgggttgt tatttttatc ag                                  32

<210> SEQ ID NO 9
<211> LENGTH: 21
<212> TYPE: DNA
<213> ORGANISM: Artificial Sequence
<220> FEATURE:
<223> OTHER INFORMATION: synthetic

<400> SEQUENCE: 9
cagctgaagc ttcgtacgct g                                              21

<210> SEQ ID NO 10
<211> LENGTH: 22
<212> TYPE: DNA
<213> ORGANISM: Artificial Sequence
<220> FEATURE:
<223> OTHER INFORMATION: synthetic
```

```
<400> SEQUENCE: 10
gcataggcca ctagtggatc tg                                    22

<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
cggggtttcg tacagtaatc agcg                                  24
```

METHOD FOR ENHANCING VANILLIN RESISTANCE OF *SACCHAROMYCES CEREVISIAE* BY KNOCKING OUT SNG1 GENE

REFERENCE TO AN ELECTRONIC SEQUENCE LISTING

The contents of the electronic sequence listing (sequence listing.txt; Size: 7,547 bytes; and Date of Creation: Dec. 10, 2020) is herein incorporated by reference in its entirety.

CROSS-REFERENCE TO RELATED APPLICATIONS

This application claims the benefit of priority from Chinese patent application No. 202010527783.4, filed on Jun. 10, 2020. The content of the aforementioned applications, including any intervening amendments thereto, is incorporated herein by reference in its entirety.

TECHNICAL FIELD

This application relates to biotechnology, and more particularly to a method for enhancing vanillin resistance of *Saccharomyces cerevisiae* by knocking out SNG1 gene.

BACKGROUND

*Saccharomyces cerevisiae* is traditionally used as an ethanol-producing strain in the fermentation industry due to its excellent activity of metabolizing hexose and high robustness under high ethanol and low pH conditions. Moreover, as a kind of type fungus, *Saccharomyces cerevisiae* has been widely explored in terms of the molecular genetics and there are numerous related operation tools and methods currently available. Therefore, *Saccharomyces cerevisiae* has become the main cell factory for fermentative production of ethanol and high-value compounds (Liu et al., 2009).

As the most abundant renewable biomass resource, lignocellulose has been extensively researched with regard to the use as raw material in the production of bioethanol or other high-value compounds. However, during the degradation of the lignocelluloses, a phenolic compound vanillin is accumulated, and its content is closely associated with the raw material and the pretreatment method. Vanillin together with other inhibitors in the lignocellulose hydrolysate, such as furfural, 5-hydroxymethyl furfural and acetic acid, can synergistically destroy the cell membrane structure, inhibit the activity of central metabolism-related enzymes, break DNA and suppress the translation initiation, thereby seriously inhibiting the microbial growth and the subsequent fermentation. In this regard, several biological detoxification methods have been designed to eliminate the inhibitory effect, but this also brings greatly increased cost. On the contrary, due to the desirable antibacterial, anti-mutagenic, anti-cancer and antiseptic activities (B e z err a et al., 2016; Kim et al., 2014), vanillin has been largely applied to the preparation of cosmetics, medicines, beverages and food additives and can bring considerable economic profit. Currently, the vanillin is produced mainly by plant extraction and artificial synthesis, where the natural vanillin is extremely expensive ($1,200-4,000 per kilogram), which is 300 times as high as the synthetic vanillin in price. Some metabolic engineering methods have been employed to construct a vanillin synthesis pathway in *Saccharomyces cerevisiae*, in which the vanillin is synthesized de novo from glucose (Furuya et al., 2017; Hansen et al., 2009). However, the produced vanillin will inhibit the subsequent vanillin synthesis due to its cytotoxicity, and specifically, 0.9 g/L vanillin will significantly inhibit the growth of *Saccharomyces cerevisiae* by extending the delay period from 2 hours to about 24 hours, prolonging the fermentation period. Considering that the commercially-available vanillin products generally have a concentration of 1 g/L or more, it is of great significance to construct a *Saccharomyces cerevisiae* mutant with improved vanillin resistance, prepare an element capable of improving the vanillin resistance or construct a *Saccharomyces cerevisiae* cell factory with high vanillin resistance. So far, there is no report about the relevance between the deletion of SNG1 gene and the improvement of vanillin resistance in *Saccharomyces cerevisiae*.

SUMMARY

An object of this application is to provide a method of enhancing vanillin resistance of *Saccharomyces cerevisiae* by knocking out SNG1 gene to overcome the defects in the prior art.

Technical solutions of this application are described as follows.

In a first aspect, this application provides a method of enhancing vanillin resistance of *Saccharomyces cerevisiae*, comprising:
  knocking out SNG1 gene from a genome of *Saccharomyces cerevisiae*.

In a second aspect, this application provides a SNG1-deletion *Saccharomyces cerevisiae* mutant, comprising a nucleotide sequence as shown in SEQ ID NO:1 consisting of, from left to right, a −18~+203 bp fragment of SNG1 gene of *Saccharomyces cerevisiae*, a nucleotide fragment of loxp-KanMX4-loxp and a +1446~+1644 bp fragment of the SNG1 gene of *Saccharomyces cerevisiae*; the −18~+203 bp fragment of SNG1 gene of *Saccharomyces cerevisiae* is shown as SEQ ID NO: 2; the nucleotide fragment of loxp-KanMX4-loxp is shown as SEQ ID NO: 4; and the +1446~+1644 bp fragment of the SNG1 gene of *Saccharomyces cerevisiae* is shown as SEQ ID NO: 3.

In a third aspect, this application provides a method of constructing the SNG1-deletion *Saccharomyces cerevisiae* mutant, comprising:
  designing the gene sequence as shown in SEQ ID NO:1 according to the SNG1 gene of a wild-type *Saccharomyces cerevisiae* strain; wherein two ends of the gene sequence shown in SEQ ID NO:1 are homologous to two ends of the SNG1 gene of the wild-type *Saccharomyces cerevisiae* strain, respectively;
  subjecting the −18~—+203 bp fragment (SEQ ID NO: 2) of the SNG1 gene and the nucleotide fragment (SEQ ID NO: 4) of loxp-KanMX4-loxp to fusion PCR to obtain a fusion PCR product;
  subjecting the fusion PCR product and the +1446~+1644 bp fragment (SEQ ID NO: 3) of the SNG1 gene to fusion PCR to obtain the gene sequence as shown in SEQ ID NO:1;
  transforming the gene sequence as shown in SEQ ID NO:1 into the wild-type *Saccharomyces cerevisiae* strain; and
  culturing the *Saccharomyces cerevisiae* strain transformed with the gene sequence as shown in SEQ ID NO:1 on a plate supplemented with 800 μg/mL of G418 to screen a transformant as the SNG1-deletion *Saccha-* romyces cerevisiae mutant, in which the SNG1 gene is replaced with the gene sequence as shown in SEQ ID NO:1;

wherein the SNG1-deletion Saccharomyces cerevisiae mutant is named as sng1Δ mutant.

In an embodiment, the method specifically comprises:

(1) extraction of genome of Saccharomyces cerevisiae BY4741 culturing Saccharomyces cerevisiae BY4741 strain in 5 mL of a YEPD liquid medium overnight; collecting Saccharomyces cerevisiae BY4741 cells; and disrupting the cells by bead grinding to extract a BY4741 genome;

(2) amplification of the fragment (SEQ ID NO: 2) homologous to a left end sequence of the SNG1 gene amplifying the fragment (SEQ ID NO: 2) by PCR using the BY4741 genome as a template and a first primer pair;

where the first primer pair consists of a

```
forward primer F1f:
                                    (SEQ ID NO: 5)
GCCGTACAGAGAACAAATATGACTAAATCGG;
and a reverse primer F1r:
                                    (SEQ ID NO: 6)
ATTAAGGGTTGTCGACCTGCAGCGTACGAAGCTTCAGCTGACAGATGACA

ATGAGGACGGC;
``` the underlined sequence is homologous to a left end sequence of the nucleotide fragment of loxp-KanMX4-loxp, for fusion PCR with the loxp-KanMX4-loxp;

(3) amplification of the fragment (SEQ ID NO: 3) homologous to a right end sequence of the SNG1 gene amplifying the fragment (SEQ ID NO: 3) by PCR using the BY4741 genome as a template and a second primer pair;

where the second primer pair consists of a

```
forward primer F2f:
                                    (SEQ ID NO: 7)
GAAGTTATTAGGTGATATCAGATCCACTAGTGGCCTATGGGAAGAAATT ACGGTATTCTCGTGGC;
and a reverse primer F2r:
                                    (SEQ ID NO: 8)
TTATTTCCGGGCGGGTTGTTATTTTTATCAG;
``` the underlined sequence is homologous to a right end sequence of the nucleotide fragment of loxp-KanMX4-loxp, for fusion PCR with the loxp-KanMX4-loxp;

(4) amplification of loxp-KanMX4-loxp (SEQ ID NO: 4)

amplifying the loxp-KanMX4-loxp by PCR using a pUG6 plasmid as template and a third primer pair;

where the third primer pair consists of a forward primer F3f: CAGCTGAAGCTTCGTACGCTG (SEQ ID NO: 9); and a reverse primer F3r: GCATAGGCCACTAGTGGATCTG (SEQ ID NO: 10);

(5) synthesis of the gene sequence shown in SEQ ID NO: 1 subjecting the fragment shown in SEQ ID NO: 2, the fragment shown in shown in SEQ ID NO: 3 and loxp-KanMX4-loxp to fusion PCR to amplify the fragment shown in SEQ ID NO: 1;

(6) transformation of the fragment shown in SEQ ID NO: 1 into wild-type Saccharomyces cerevisiae BY4741 subjecting the fragment shown in SEQ ID NO: 1 to gel purification; transforming the fragment shown in SEQ ID NO: 1 into Saccharomyces cerevisiae BY4741; and culturing Saccharomyces cerevisiae BY4741 on a YEPD plate containing 800 μg/mL of G418 to screen a transformant as a preliminary SNG1-deletion Saccharomyces cerevisiae mutant, which is named as sng1Δ mutant; and (7) PCR identification picking a single colony from the YEPD plate; culturing the single colony in a YEPD liquid medium supplemented with 200 μg/mL of G418 at 30° C. and 200 rpm for 24 h to produce a suspension; extracting genome from cells in the suspension; and subjecting fourth primer pairs to PCR amplification using the genome as template for identification;

where the fourth primer pairs consist of a forward primer Fy: CGGGGTTTCGTACAGTAATCAGCG (SEQ ID NO: 11); and a reverse primer F2r: TTAATTTCCGGGCGGGTTGTTATTTTTATCAG; the forward primer Fy is designed according to a +87~+110 region of the SNG1 gene;

in the PCR identification, a genome extracted from wild-type Saccharomyces cerevisiae BY4741 is used as positive control; a 1558 bp fragment is obtained when the positive control is used as template; if the 1558 bp fragment is missing in the PCR product using the genome of the transformant as template, it indicates that the SNG1 gene has been successfully knocked out. Therefore, it cannot obtain related nucleotide fragment through PCR using the genome of the desired sng1Δ mutant as template.

In a fourth aspect, this application further provides a use of the gene sequence shown in SEQ ID NO: 1 in the construction of Saccharomyces cerevisiae with high vanillin resistance.

The SNG1-deletion Saccharomyces cerevisiae mutant provided herein has been experimentally demonstrated to have greatly-improved vanillin resistance, and the lag phase and the fermentation period under vanillin stress are significantly shortened, which provides theoretical reference for the construction of high vanillin-resistance Saccharomyces cerevisiae cells.

Specifically, the sng1Δ mutant and the wild-type strain BY4741 are separately cultured on a YEPD plate supplemented with 6 mmol/L of vanillin to observe their growth conditions, and the results reveal that the sng1Δ mutant has superior growth status to the control strain. When cultured aerobically in a SC medium containing 6 mmol/L of vanillin under shaking, the sng1Δ mutant has a maximum specific growth rate of 0.225/h, which is 70% higher than that of the control strain. The detoxification pathway of vanillin in Saccharomyces cerevisiae is to reduce the vanillin to low-toxic vanillyl alcohol, so the reducing rate of vanillin is positively correlated with the vanillin resistance. The results demonstrate that the sng1Δ mutant can quickly reduce vanillin to vanillyl alcohol at a maximum specific reduction rate of 0.052 g g$^{-1}$ h$^{-1}$, which is improved by 48% compared to the control strain.

Compared to the prior art, this application has the following beneficial effects.

This application provides a SNG1-deletion Saccharomyces cerevisiae mutant (sng1Δ mutant) for the first time, which is superior to the wild-type strain in the maximum specific growth rate and the specific reduction rate of vanillin under vanillin stress. Due to the desirable vanillin resistance, the sng1Δ mutant is suitable for the fermentation of lignocellulose hydrolysate, and the biological detoxification procedure is not required any more, lowering the production cost. At the same time, the sng1Δ mutant is also a dominant strain for the production of vanillin or vanillyl alcohol, and thus has a considerable application value. Moreover, as further confirmed by experiments, the sng1Δ mutant shows similar growth pattern to the control strain under stress-free conditions; while in the presence of vanillin, compared to the control strain, the sng1Δ mutant is improved by 70% and 52% respectively in the maximum specific growth rate and the specific reduction rate of vanillin, which further indicates that this mutant can be applied to the production of vanillin or vanillyl alcohol and the production of bioethanol or other high-value compounds from lignocelluloses.

DETAILED DESCRIPTION OF EMBODIMENTS

Figure 1:
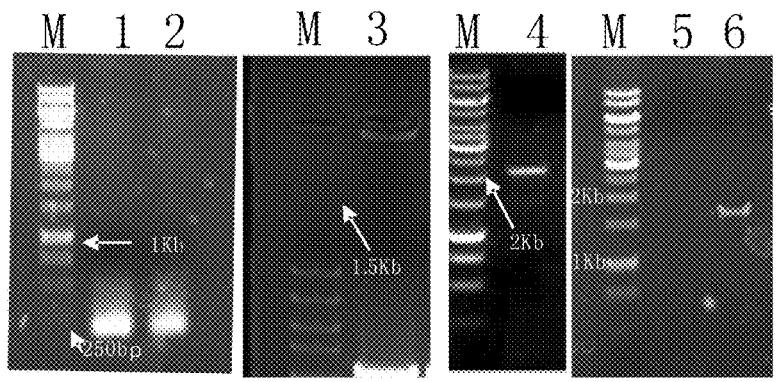
FIG. 1 is a gel electrophoresis image showing nucleotide fragments involved in the construction of a sng1Δ mutant, where M: marker; 1: the nucleotide fragment shown in SEQ ID NO: 2; 2: the nucleotide fragment shown in SEQ ID NO: 3; 3: loxp-KanMX4-loxp; 4: the nucleotide fragment shown in SEQ ID NO: 1; 5: amplified product using genome of the sng1Δ mutant as template (the absence of the target sequence indicates that the SNG1 has been successfully knocked out; and 6: amplified product using genome of the wild-type strain (positive control).

The disclosure will be described in detail below with reference to the embodiments and accompanying drawings. Provided below are merely preferred embodiments of the disclosure, and it should be noted that these embodiments are merely illustrative of the disclosure, and are not intended to limit the disclosure. Any modification, change and replacement made by those skilled in the art without departing from the spirit of the disclosure should fall within the scope of the disclosure.

Experimental Materials (1) Liquid YEPD (Yeast extract Peptone Dextrose) medium for *Saccharomyces cerevisiae:* 20 g/L of peptone, 10 g/L of yeast extract and 20 g/L of glucose. 20 g/L of agar was required to prepare a solid YEPD medium. The medium was sterilized at 115° C. for 30 min immediately after the preparation. G418 with a final concentration of 800 μg/mL may be introduced for the purpose of screening.

Synthetic complete (SC) medium for yeast: 6.7 g/L of yeast nitrogen base, 5 g/L of ammonium sulfate, 0.77 g/L of CSM-URA, supplemented with uracil to a final concentration of 20 mg/L. After sterilized at 115° C. for 30 min, the medium was further supplemented with a pre-sterilized 400 g/L glucose mother liquor to a final concentration of 20 g/L.

(2) Enzymes and reagents

The DNA polymerase used in PCR was Phata Max Super Fidelity DNA Polymerase P505-d2, which was purchased from Nanjing Vazyme Biotech Co., Ltd.

(3) Strain and plasmid

*Saccharomyces cerevisiae* BY4741 was purchased from a website platform (http://www.miaolingbio.com). The pUG6 plasmid was constructed according to the method mentioned in a literature (A new efficient gene disruption cassette for repeated use in budding yeast[J]. *Nucleic Acids Res,* 1996, 24(13): 2519-2524).

Unless otherwise specified, other materials and reagents are commercially available.

Example 1 Construction of Sng1Δ Mutant (1) Extraction of Genome of *Saccharomyces cerevisiae* BY4741

*Saccharomyces cerevisiae* BY4741 was inoculated to 5 mL of a YEPD medium and cultured at 30° C. and 200 rpm overnight. The suspension was centrifuged to collect *Saccharomyces cerevisiae* cells, which were washed with 1 mL of sterile water and then suspended with 200 μL of lysis buffer, where the lysis buffer contained 2% Triton X-100, 1% SDS, 100 mmol/L of NaCl, 10 mmol/L of Tris-HCl and 1 mmol/L of EDTA, and was adjusted to pH 8.0. The cells suspension was transferred to a screw-capped tube containing 0.4 g of glass beads, to which 200 μL of a mixture of phenol, chloroform and isoamyl alcohol (25:24:1) was added. After vortexed for 3 min, the reaction mixture was added with 200 μL of TE solution, mixed uniformly and centrifuged at 4° C. and 13,000 rpm for 10 min. The supernatant was transferred to a new Eppendorf tube, to which 1 mL of absolute ethanol (−20° C.) was added to precipitate the DNA. The Eppendorf tube was centrifuged at 4° C. and 13,000 rpm for 10 min, and the supernatant was discarded. The DNA precipitate was dried under vacuum, dissolved with 400 μL of TE solution and added with 10 μL of RNase A (10 mg/mL). The reaction mixture was incubated at 37° C. for 15 min, added with 10 μL of ammonium acetate (4 mol/L) and 1 mL of absolute ethanol, mixed uniformly and centrifuged at 13,000 rpm for 10 min. The supernatant was discarded, and the precipitate was dried and dissolved with 50 μL of ddH$_2$O to obtain the genome of *Saccharomyces cerevisiae* BY4741.

(2) Amplification of the Fragment Shown in SEQ ID NO: 2

The fragment shown in SEQ ID NO: 2 was amplified by PCR using the genome of *Saccharomyces cerevisiae* BY4741 as template and a first primer pair, where the first primer pair consisted of a forward primer F1f:
GCCGTACAGAGAACAAATATGACTAAATCGG;
and a reverse primer F1r:
ATTAAGGGTTGTCGACCTGCAGCGTACGAAGCTTCAGCTGACAGATGACA

ATGAGGACGGC.

The underlined fragment was homologous to a left end sequence of the loxp-KanMX4-loxp fragment, for fusion PCR with loxp-KanMX4-loxp. The PCR system consisted of 0.5 μL of template, 0.5 μL of the forward primer F1f, 0.5 μL of the reverse primer F1r, 2 μL of dNTPs, 0.5 μL of DNA Polymerase, 25 μL of 2×buffer and 21 μL of ddH$_2$O, and the PCR amplification was programmed as follows: pre-denaturation at 95° C. for 3 min; 30 cycles: denaturation at 95° C. for 15 s, annealing at 55° C. for 15 s and extension at 72° C. for 10 s; and final extension at 72° C. for 5 min.

(3) Amplification of the Fragment Shown in SEQ ID NO: 3

The fragment shown in SEQ ID NO: 3 was amplified by PCR using the genome of Saccharomyces cerevisiae BY4741 as template and a second primer pair, where the second primer pair consisted of a

```
forward primer F2f:
GAAGTTATTAGGTGATATCAGATCCACTAGTGGCCTATGGGAAGAAATT
ACGGTATTCTCGTGGC;
and a reverse primer F2r:
TTAATTTCCGGGCGGGTTGTTATTTTTATCAG.
```

The underlined fragment was homologous to a right end sequence of the loxp-KanMX4-loxp fragment, for fusion PCR with loxp-KanMX4-loxp. The PCR system consisted of 0.5 μL of template, 0.5 μL of the forward primer F2f, 0.5 μL of the reverse primer F2r, 2 μL of dNTPs, 0.5 μL of DNA Polymerase, 25 μL of 2×buffer and 21 μL of ddH$_2$O, and the PCR amplification was programmed as follows: pre-denaturation at 95° C. for 3 min; 30 cycles: denaturation at 95° C. for 15 s, annealing at 55° C. for 15 s and extension at 72° C. for 10 s; and final extension at 72° C. for 5 min.

(4) Amplification of the Loxp-KanMX4-Loxp Fragment Shown in SEQ ID NO: 4

The loxp-KanMX4-loxp fragment was amplified by PCR using a pUG6 plasmid as template and a third primer pair, where the third primer pair consisted of a forward primer F3f: CAGCTGAAGCTTCGTACGCTG; and a reverse primer F3r: GCATAGGCCACTAGTGGATCTG. The PCR system consisted of 0.5 μL of template, 0.5 μL of the forward primer F3f, 0.5 μL of the reverse primer F3r, 2 μL of dNTPs, 0.5 μL of DNA Polymerase, 25 μL of 2×buffer and 21 μL of ddH$_2$O, and the PCR amplification was programmed as follows: pre-denaturation at 95° C. for 3 min; 30 cycles: denaturation at 95° C. for 15 s, annealing at 55° C. for 15 s and extension at 72° C. for 45 s; and final extension at 72° C. for 5 min.

(5) Amplification of the Gene Sequence Shown in SEQ ID NO: 1

The gene sequence shown in SEQ ID NO: 1 was amplified by fusion PCR using SEQ ID NO: 2, loxp-KanMX4-loxp and SEQ ID NO: 3 as templates and the second primer pair, where the fusion PCR system consisted of 0.5 μL of SEQ ID NO: 2, 0.5 μL of loxp-KanMX4-loxp, 0.5 μL of SEQ ID NO: 3, 0.5 μL of the forward primer F2f, 0.5 of the reverse primer F2r, 2 μL of dNTPs, 0.5 μL of DNA Polymerase, 25 μL of 2×buffer and 20 μL of ddH$_2$O, and the PCR amplification was programmed as follows: pre-denaturation at 95° C. for 3 min; 30 cycles: denaturation at 95° C. for 15 s, annealing at 55° C. for 15 s and extension at 72° C. for 1 min; and final extension at 72° C. for 5 min.

(6) Transformation of SEQ ID NO: 1 into Wild-Type Saccharomyces cerevisiae Strain The nucleotide fragment shown in SEQ ID NO: 1 was subjected to gel purification, and the specific process was described as follows. The PCR products were subjected to agarose gel electrophoresis, and the resulting gel was collected and placed under ultraviolet light. The gel slice with target DNA was carefully excised, placed in an Eppendorf tube and weighed. The recovery and purification of DNA fragments in the agarose gel were carried out as instructed by E.Z.N.A Gel Extraction kit (Omega Bio-tek, Co., Ltd, USA).

The purified nucleotide fragment shown in SEQ ID NO: 1 was transformed into wild-type Saccharomyces cerevisiae cells by lithium acetate protocol. Specifically, a single colony was picked and cultured in 1-2 mL of YEPD medium overnight, and then the cells were transferred to 40 mL of YEPD medium at an initial OD$_{600}$ of 0.2 and cultured at 30° C. under shaking to OD$_{600}$ of 0.6-1.0. The cell suspension was centrifuged to collect the cells, which were then washed with sterile water, resuspended with 1 mL of 0.1 mol/L LiAc and transferred to a new sterile Eppendorf tube. The resuspension was centrifuged, and the supernatant was discarded. The cells were collected and resuspended with 400 μL of 0.1 mol/L LiAc, and the resulting suspension was divided into multiple 50 μL aliquots, which were respectively transferred to multiple sterile Eppendorf tubes, respectively. After centrifugation, the supernatant was discarded, and each Eppendorf tube was sequentially added with 240 μL of 50% (w/v) PEG-3350, 36 μL of 1 mol/L LiAc and 10 μL of 10 mg/mL single-stranded salmon sperm DNA (boil for 5 min before use, then quickly place on ice; use within half an hour) and a total of 70 μL of sterile re-distilled water and a plasmid (or DNA fragment), shaken, incubated at 30° C. for 30 min and subjected to heat shock in a 42° C. water bath for 25 min. Then the Eppendorf tube was centrifuged, and the supernatant was discarded. The cells were resuspended with YEPD medium and incubated for 2-4 h. The resuspension was centrifuged again, and the cells were suspended with sterile water and spread onto a YEPD plate supplemented with 800 μg/mL of G418 for screening to preliminarily obtain a SNG1-deletion S. cerevisiae mutant, which was named as sng1.4 mutant.

(7) PCR Identification

A single colony was picked from the plate and cultured in a YEPD liquid medium containing 200 μg/mL of G418 at 30° C. and 200 rpm for 24 h. Then the genome was extracted according to the procedure of extraction of BY4741 genome and was identified by PCR, where the obtained genome was used as template. The forward primer was Fy (CGGGGTTTCGTACAGTAATCAGCG), which was designed according to the +87~+110 region of the SNG1 gene; and the reverse primer was F2r (TTAATTTCCGGGCGGGTTGTTATTTTTATCAG).

The electrophoresis (FIG. 1) results confirmed that a 1558 bp fragment can be amplified when using the genome of the wild-type BY4741 (positive control) as template, so the absence of the 1558 bp fragment in the amplified product indicated that the SNG1 gene had been successfully knocked out, that was, the 1558 bp fragment was absent in the amplified product when using the genome of the sng1.4 mutant as template.

The PCR system consisted of 0.5 μL of template, 0.5 μL of forward primer Fy, 0.5 μL of reverse primer F2r, 2 μL of dNTPs, 0.5 μL of DNA Polymerase, 25 μL of 2×buffer and 21 μL of ddH$_2$O, and the PCR was programmed as follows: pre-denaturation at 95° C. for 3 min; 30 cycles: denaturation at 95° C. for 15 s, annealing at 55° C. for 15 s and extension at 72° C. for 15 s; and final extension at 72° C. for 5 min.

Example 2 Verification of Vanillin Resistance (Tolerance) of sng1Δ Mutant (1) Test on Vanillin Resistance of Sng1Δ Mutant The sng1Δ mutant obtained above was cultured on a YEPD plate containing 6 mmol/L of vanillin to observe its growth status. Specifically, the sng1Δ mutant was inoculated to 1-2 mL of a liquid YEPD medium and cultured at 30° C. overnight to logarithmic growth phase. Then the mutant cells were transferred to 5 mL of fresh medium at an initial $OD_{600}$ of 0.2, cultured overnight and centrifuged. The cells were collected, washed with 1 mL of sterile water three times and centrifuged at 8,000 r/min. The cells were again suspended with sterile water and placed at 30° C. for 9 h to prepare resting cells, and during the preparation, the medium was prepared, poured to a plate and naturally dried. The cell suspension was adjusted to $OD_{600}$ of 1.0 and subjected to 10-fold serial dilution, and 4 μL of the suspension at each dilution was dropped on the plate, cultured at 30° C. for 1-3 days and photographed to observe the colony growth. The control strain was tested in the same way for the vanillin resistance.

Figure 2:
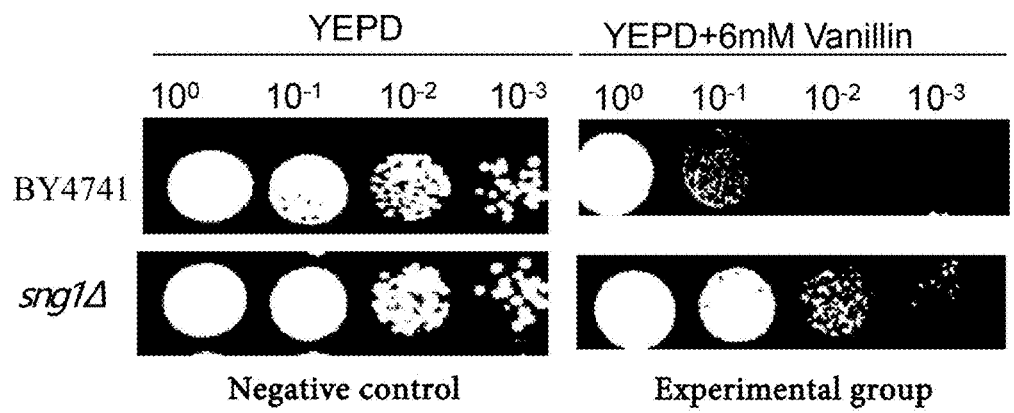
FIG. 2 illustrates growth statuses of the sng1Δ mutant and the wild-type strain on YEPD plate.

The results were presented in FIG. 2, in which it can be obviously seen that the sng1Δ mutant displayed a superior growth status to the control strain under vanillin stress.

(2) Shake-Flask Fermentation

A single colony of the sng1Δ mutant was picked, transferred to 1-2 mL of a SC medium and cultured at 30° C. and 200 rpm for about 24 h. The cell suspension was transferred to 20 mL of fresh medium at an initial $OD_{600}$ of 0.2 and cultured at 30° C. and 200 rpm overnight to the mid log phase for secondary activation. Then the cell culture, at an initial $OD_{600}$ of 0.2, was transferred to 40 mL of a SC medium containing 6 mmol/L of vanillin and cultured at 30° C. and 200 rpm under shaking, where the $OD_{600}$ was regularly measured.

Figure 3:
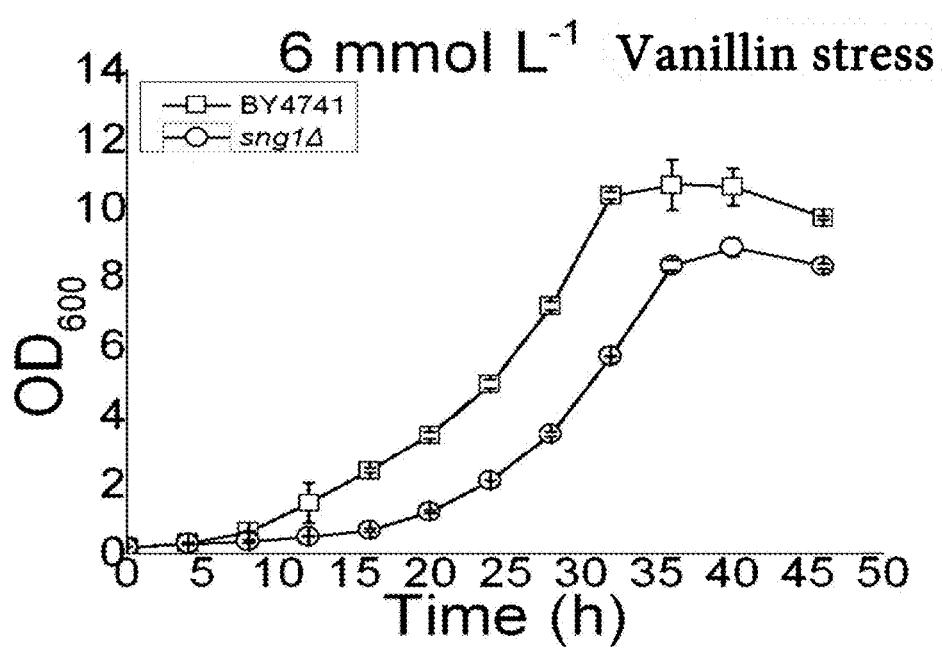
FIG. 3 shows growth statuses of the sng1Δ mutant and the wild-type strain under vanillin stress during the shake-flask fermentation.

The maximum specific growth rate was obtained by calculating a near regression slope of $\ln(OD_{600})$ versus time in the logarithmic growth phase. As shown in FIG. 3, the sng1Δ mutant showed a maximum specific growth rate of 0.225/h under vanillin stress.

After measured for $OD_{600}$, the cell culture was centrifuged, and the supernatant was collected and analyzed by HPLC to determine the extracellular vanillin content.

The HPLC method for the determination of vanillin was described as follows.

The fermentation liquid was centrifuged at 13,000 r/min for 10 min, and the supernatant was collected, filtered with a 0.45 μm microporous membrane and then analyzed by HPLC for extracellular metabolites, where HPLC conditions were listed as follows: photodiode array detector (SPD-M20A); BioSil-C18 column (Bio-Rad, USA); mobile phase: 40% methanol; flow rate: 0.6 mL/min; temperature: room temperature; and detection wavelength: 210 nm.

The specific consumption rate of vanillin was calculated based on the cell dry weight, which was determined as follows. 10 mL, 20 mL, 30 mL, 40 mL and 50 mL of the culture medium were taken, measured for OD 600 and filtered with a 0.45 μm nitrocellulose filter membrane (weighed in advance), respectively. Then the filter membrane was washed twice with deionized water, dried in a microwave oven at 360 W for 20 min and weighed, and the cell dry weight can be obtained according to the weight difference of the filter membrane. The $OD_{600}$ of cells in the culture medium was a product of one unit of $OD_{600}$ and the volume. A curve of $OD_{600}$ versus cell dry weight was plotted, and the cell dry weight during the fermentation process can be calculated according to this curve. For the BY4741 strains, one unit of $OD_{600}$ corresponded to a cell dry weight of 0.18 g/L. The specific consumption rate of vanillin was calculated according to the following equation:

$$r = \frac{A_n - A_m}{\frac{1}{2}\sum_{i=m+1}^{n}(B_1 + B_{i-1}) \times (t_i - t_{i-1})};$$

where, r: specific consumption/production rate of a certain substance during the period from sampling point m to n; A: metabolite concentration at sampling points n, i and m; B: biomass concentration at sampling points n, i and m; t: time at sampling points n, i and m; and specific consumption/production rate: $g\ g^{-1}\ h^{-1}$.

Figure 4:
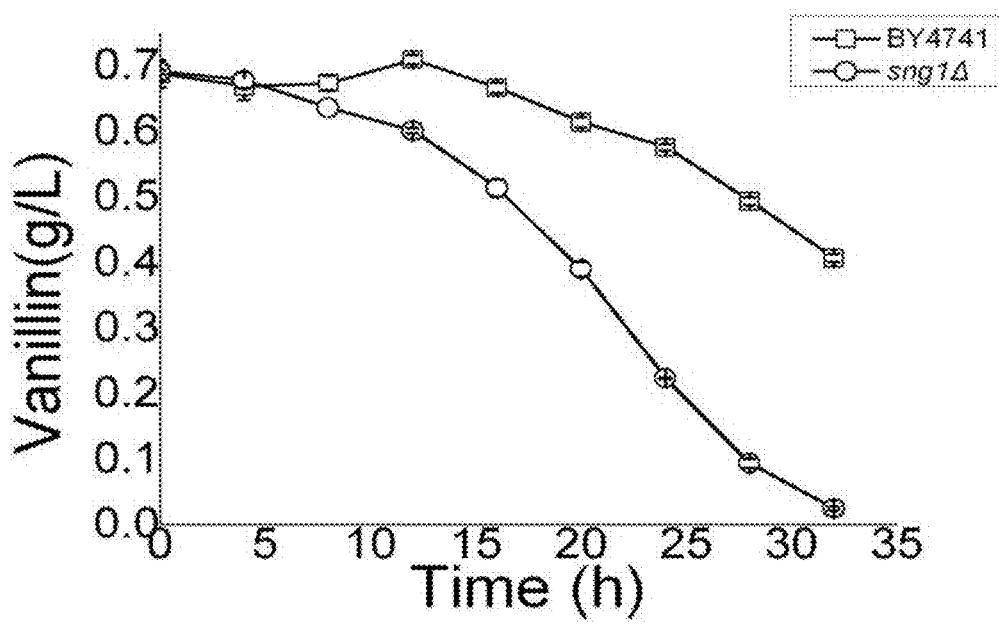
FIG. 4 shows the ability of the sng1Δ mutant and the wild-type strain to metabolize vanillin.

The specific consumption rate of vanillin in the sng1Δ mutant was 0.052 $g\ g^{-1}\ h^{-1}$ (FIG. 4).

The wild-type BY4741 strain was also subjected to shake flask fermentation according to the above operation, and its maximum specific growth rate was calculated to be 0.132 $h^{-1}$ using the method by which the maximum specific growth rate of the sng1Δ mutant was calculated (FIG. 3). Similarly, the specific consumption rate of vanillin in the wild-type BY4741 strain was calculated to be 0.035 $g\ g^{-1}\ h^{-1}$ according to the above method (FIG. 4).

The sng1Δ mutant was subjected to shake flask fermentation in a SC medium without vanillin stress, and the operation process was the same as above. In this case, the sng1Δ mutant had a maximum specific growth rate of 0.293 $h^{-1}$ (FIG. 5).

Figure 5:
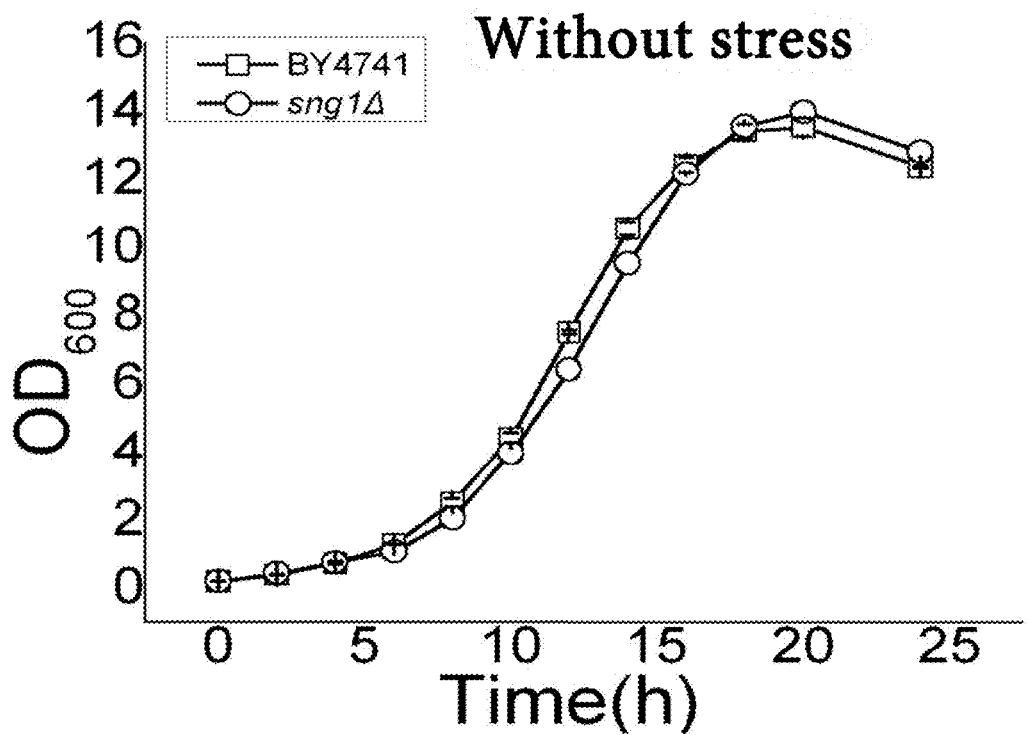
FIG. 5 illustrates the growth statuses of the sng1Δ mutant and the wild-type strain under normal conditions during the shake-flask fermentation.

The wild-type BY4741 strain was also subjected to stress-free shake flask fermentation according to the above process, and showed a maximum specific growth rate of 0.304 $h^{-1}$ (FIG. 5).

It can be seen from the above that in the absence of vanillin, there was no significant difference between the sng1Δ mutant and the wild-type BY4741 strain in the growth; while under vanillin stress, compared to the control strain, the sng1Δ mutant was improved by 70% and 52% respectively in the maximum specific growth rate and the specific consumption rate of vanillin.

What is claimed is:

1. A mutant SNG1 gene, comprising the nucleotide sequence of SEQ ID NO: 1.

2. A *Saccharomyces cerevisiae* cell with vanillin resistance, the *Saccharomyces cerevisiae* cell comprising a mutant SNG1 gene comprising the nucleotide sequence of SEQ ID NO: 1.

* * * * *